United States Patent [19]

Kiesser et al.

[11] Patent Number: 5,739,091
[45] Date of Patent: Apr. 14, 1998

[54] ENZYME GRANULATES

[76] Inventors: Torsten W. Kiesser, An Der Alpheide 49; Hubert A. Herrmann, Celler Str. 116, both of D-31852 Nienburg/Weser; Gerhard Konieczny-Janda, Schoeneberger Str. 23, D-30982 Pattensen, all of Germany

[21] Appl. No.: 392,972

[22] PCT Filed: Aug. 5, 1993

[86] PCT No.: PCT/EP93/02081

§ 371 Date: Apr. 14, 1995

§ 102(e) Date: Apr. 14, 1995

[87] PCT Pub. No.: WO94/04665

PCT Pub. Date: Mar. 3, 1994

[30] Foreign Application Priority Data

Aug. 14, 1992 [DE] Germany ..................... 42 26 923.7

[51] Int. Cl.$^6$ .............. C11D 3/00; C11D 17/06; C12N 9/96; C12N 9/98
[52] U.S. Cl. ............ 510/224; 435/187; 435/188; 510/226; 510/300; 510/305; 510/320; 510/323
[58] Field of Search ...................... 435/187, 188; 252/174.12, 174, DIG. 12, 174.21; 510/224, 226, 320, 300, 305, 323

[56] References Cited

U.S. PATENT DOCUMENTS

| | | |
|---|---|---|
| 4,242,219 | 12/1980 | Bogerman et al. |
| 4,515,705 | 5/1985 | Moeddel .................... 252/174.12 |
| 4,548,744 | 10/1985 | Connor et al. ............... 252/545 |
| 4,561,991 | 12/1985 | Herbots et al. .............. 252/118 |
| 4,661,287 | 4/1987 | Crossin ....................... 252/174.12 |
| 4,715,990 | 12/1987 | Crossin ....................... 252/174.12 |
| 4,759,876 | 7/1988 | Crossin ....................... 252/174.12 |
| 5,178,789 | 1/1993 | Estell ......................... 252/174.12 |
| 5,269,960 | 12/1993 | Gray et al. ................... 252/174.12 |
| 5,422,030 | 6/1995 | Panandiker et al. .......... 252/174.12 |

FOREIGN PATENT DOCUMENTS

| | | |
|---|---|---|
| 170360 | 2/1986 | European Pat. Off. |
| 256127 | 2/1988 | European Pat. Off. |
| 2831778/8 | 1/1979 | Germany |
| 2186883 | 8/1987 | United Kingdom |
| WO 91/09941 | 7/1991 | WIPO |
| WO 91/09943 | 7/1991 | WIPO |
| WO 92/11347 | 7/1992 | WIPO |

*Primary Examiner*—Herbert J. Lilling
*Attorney, Agent, or Firm*—Cooley Godward LLP

[57] ABSTRACT

Enzyme granules which comprise in their composition, in addition to the enzyme, water-soluble and water-insoluble fillers, binders and if appropriate other granulating auxiliaries, a formate of an alkali metal or alkaline earth metal and if appropriate reducing sugars being added to them to stabilize the enzyme, are described. All the enzymes customary for detergents and cleaning purposes, in particular alkaline proteases, can be processed into the enzyme granules. A process for the preparation of these enzyme granules and their use in pulverulent detergent formulations are also described.

16 Claims, No Drawings

ENZYME GRANULATES

DESCRIPTION

The present invention relates to novel enzyme granules, a process for their preparation and their use in detergent and cleaning agent compositions.

Enzymes are employed in numerous detergent compositions, for example for cleaning textiles or kitchen utensils, to increase the washing activity. Proteases, lipases, amylases or cellulases are the enzymes commonly employed in this context. The enzymes are added to pulverulent detergent formulations in the form of so-called enzyme granules, which comprise the enzyme or enzyme mixture in question together with a filler and if appropriate other granulating auxiliaries. Such enzyme granules are usually obtained by processing an enzyme concentrate with fillers and binders and if appropriate also other granulating auxiliaries to a composition and granulating the composition. The resulting granule particles are then dried and, if appropriate, coated with a protective coating, and can then be employed in pulverulent detergent formulations.

There continues to be a need for enzyme granules which have an improved storage stability, especially in the presence of customary detergent constituents, and good solution properties.

There was thus the object of providing novel enzyme granules which have a high storage stability and good solution properties and which are particularly suitable for use in pulverulent detergent formulations.

Enzyme granules which display the required properties have now been found.

The invention thus relates to enzyme granules comprising an enzyme or enzyme mixture, a water-insoluble filler mixture, water-soluble filler mixtures, binders and, if appropriate, other granulating auxiliaries, the granules comprising a formate of an alkali metal or alkaline earth metal and if appropriate reducing sugars.

The storage stability of the enzymes processed in the granules according to the invention is increased in a surprising manner by addition of formate of an alkali metal or alkaline earth metal, it being possible for the stabilizing action of the formate of an alkali metal or alkaline earth metal to be increased still further in a synergistic manner, if desired, by addition of reducing sugars. The formate of an alkali metal or alkaline earth metal is therefore preferably always employed in the granules according to the invention in combination with reducing sugars.

The amount of formate of an alkali metal or alkaline earth metal in the enzyme granules according to the invention should preferably be 0.5 to 15% by weight, preferably 1 to 8% by weight, based on the total solids content. Alkaline earth metal formates here can either be added as such or be formed in situ from an alkali metal formate, in particular sodium formate, and a water-soluble alkaline earth metal salt, in particular a calcium salt. Calcium formate is particularly preferably employed in the stated amounts in the enzyme granules according to the invention.

If reducing sugars are to be used, where appropriate, for synergistic intensification of the stabilizing action of the formate of an alkali metal or alkaline earth metal employed in the enzyme granules according to the invention, reducing sugars which are advantageously employed are monosaccharides, such as glucose, or disaccharides, such as lactose and/or maltose, or polysaccharides, such as dextrins. Mixtures of reducing sugars, such as, for example, glucose syrup, are also suitable. Disaccharides, in particular lactose and/or maltose, are preferably used in the enzyme granules according to the invention. The abovementioned reducing sugars are advantageously employed in the enzyme granules according to the invention in an amount of 0.5 to 20% by weight, in particular 2.0 to 10.0% by weight, based on the total solids content.

The enzyme granules according to the invention can comprise, as enzymes, all the enzymes customary in detergent and cleaning agent compositions, for example enzymes such as proteases, lipases, amylases, glucanases, such as cellulases, hemicellulases or pullulanases, or oxidoreductases, preferably amylases, cellulases, lipases or proteases. The enzyme granules according to the invention can comprise the enzymes individually or also as enzyme mixtures, for example as protease/amylase mixtures or protease/lipase mixtures.

In a particularly preferred embodiment, the enzyme granules according to the invention comprise proteases, in particular alkaline proteases. The proteases which have improved properties, such as an increased washing performance or improved stability due to chemical and/or genetic engineering modifications, can also be incorporated into the enzyme granules according to the invention in particular here in an advantageous manner. Advantageous alkaline proteases here are, in particular, the so-called subtilisins. Subtilisins are alkaline proteases having a pH optimum in the alkaline pH range and an essential serine radical in the active centre. They can be isolated in a known manner from Gram-positive bacteria or fungi. The subtilisins isolated from the bacillus strains are preferred here, for example subtilisins such as subtilisin BPN'-, subtilisin Carlsberg and the subtilisins which can be isolated from *Bacillus subtilus, Bacillus amyloliquefaciens, Bacillus licheniformis, Bacillus lentus, Bacillus mesentericus* or *Bacillus alcalophilus*. Subtilisins which have a pH optium in the range of 7–13 and that are commercially obtainable, for example, as Savinase®, Maxacal®, Durazym®, Maxapem® or Opticlean® are particularly preferred.

The enzymes suitable for the enzyme granules according to the invention can be isolated from suitable microorganisms, especially from bacteria or fungi, by fermentation processes in a manner known per se. The fermenter broths obtained during the fermentation are freed from insoluble concomitant substances, for example by filtration, and then concentrated in a manner known per se, for example by membrane filtration processes, such as micro- and/or ultrafiltration with subsequent dialysis, if appropriate, and/or by thin-film evaporation. So-called enzyme concentrates which usually comprise the enzyme or enzyme mixture in an amount of 2 to 50% by weight, based on the dry matter, in addition to any other concomitant substances which have not been removed, are thus obtained. If desired, these liquid enzyme concentrates can be converted further into dry enzyme concentrates, for example by spray drying and/or freeze drying.

The water-insoluble filler mixture contained in the enzyme granules according to the invention usually comprises a mixture of cellulose and a laminar silicate or laminar silicate mixture, if appropriate cereal flour and/or starch also being other constituents of the water-insoluble filler mixture in a preferred embodiment. Cereal flour and starch can be employed here either by themselves or as a mixture with one another. Cereal flours which can be used here are all the flours known per se, from wheat, rye, barley, oats, rice or maize. Wheat flour is preferably employed.

The cellulose constituent in the water-insoluble filler mixture consists of fibrous cellulose, for example fibrous cellulose having an average fibre length in the range of about 20 to 50 μm. Fibrous cellulose having an average fibre length of about 30 μm has proved to be particularly preferably suitable.

The water-insoluble filler mixture comprises, as other components, laminar silicates, such as bentonite or kaolin or laminar silicate mixtures of kaolin and bentonite. If appropriate, the granules can also comprise kaolin as a mixture with calcium carbonate and/or bentonite.

The enzyme granules according to the invention usually comprise, as water-soluble filler mixtures, inorganic water-soluble salts such as, for example, alkali metal chlorides, alkali metal acetates, alkali metal sulphates or mixtures thereof. The alkali metal sulphates, in particular sodium sulphate, are preferred.

The enzyme granules according to the invention comprise, as binders, binders from the group consisting of polyethylene glycol, in particular polyethylene glycols having molecular weights in the range from 200 to 10.000 and/or polyvinylpyrrolidone, in particular polyvinylpyrrolidone having molecular weights in the range from 12,000 to 3,000,000, preferably 1,300,000 to 2,800,000. If appropriate, only polyethylene glycol can be added as the binder.

The enzyme granules according to the invention can be of a composition such that, for example, in each case based on the total solids content, the water-insoluble filler mixture comprises 15 to 40% by weight of cellulose, 5 to 18% by weight of kaolin, if desired as a mixture with 1 to 35% by weight of bentonite and 1 to 13% by weight of calcium carbonate. If appropriate, the granules can also comprise, as water-insoluble fillers, 0 to 10% by weight of cereal flour and/or 0 to 50% by weight of starch. 0.5 to 20% by weight of sodium sulphate are usually employed as the water-soluble fillers. Furthermore, the granules can comprise up to 30% by weight of binders from the group consisting of polyethylene glycol and polyvinylpyrrolidone. The enzyme can be present in the enzyme granules according to the invention as an enzyme concentrate in an amount of 1 to 40% by weight, which has been prepared in a manner known per se, as described above. According to the invention, the granules can comprise 0.5 to 15% by weight of a formate of an alkali metal or alkaline earth metal and if appropriate 0.5 to 20% by weight of reducing sugars, in particular reducing disaccharides, for stabilization of the enzymes.

In a preferred embodiment, enzyme granules according to the invention comprise, in each case based on the total solids content, 10 to 20% by weight of enzyme concentrate, 20 to 30% by weight of cellulose, 0 to 8% by weight of cereal flour and/or 0 to 20% by weight of starch, 10 to 15% by weight of kaolin, 5 to 12% by weight of calcium carbonate, 10 to 15% by weight of sodium sulphate, 0.5 to 2% by weight of polyvinylpyrrolidone (molecular weight 1,300,000), 10 to 15% by weight of polyethylene glycol (molcular weight 3,000), 2.0 to 10% by weight of lactose and 1 to 8% by weight of calcium formate.

The enzyme granules according to the invention can of course also comprise other granulating auxiliaries, such as, for example, lubricants or dispersing auxiliaries, in addition to the abovementioned main constituents. A lubricant which can be used, is, for example, a glycerol monoester with long-chain fatty acids, and a dispersing auxiliary which can be used is, for example, a sulphosuccinic acid ester with long-chain fatty alcohols, in concentrations of up to 10% by weight.

The invention furthermore relates to a process for the preparation of enzyme granules in which an extrudable composition obtained by mixing an enzyme concentrate with water, fillers, binders, and if appropriate other constituents is extruded to particles, the resulting particles are rounded in a rounding apparatus, and the rounded particles are then dried and, if appropriate, covered with a protective coating, a formate of an alkali metal or alkaline earth metal, preferably calcium formate, in an amount of 0.5 to 15% by weight and, if appropriate, reducing sugars, preferably lactose and/or maltose, in an amount of 0.5 to 20% by weight, based on the total solids content of the enzyme granules, being added to the extrudable composition.

Enzyme concentrates which can be employed in the process according to the invention are liquid enzyme concentrates such as are obtained in a manner known per se by fermentation of microorganisms and working up of the fermenter broths obtained during fermentation. Enzyme concentrates in the context of the invention are also understood as meaning, however, solid enzyme concentrates, such as can be obtained, for example, by the freeze-drying of liquid enzyme concentrates.

The process is expediently carried out by a procedure in which the enzyme concentrate is added to a previously prepared dry pre-mix of the other pulverulent constituents of the recipe in a suitable mixing apparatus, for example a cone mixer or plough lathe mixer. Water is then metered in to the extent that a composition which can be easily shaped and extruded is formed. The moisture content of this mixture is usually 10 to 40% by weight. The extrudable composition thus obtained is mixed in the mixture until homogeneous and then passed to an extruder. In the extruder, the composition is extruded through a perforated disc having hole diameters of 0.4 to 3 mm, preferably 0.6 mm, to give extrudates, which are then rounded to spherical particles on a rounding apparatus, for example a rotary plate apparatus. After rounding, the still moist particles are dried to a residual moisture content of 10 to 2% at a temperature of 30° C. to 50° C. in a drying unit, for example a fluidized bed drying unit. If desired, the resulting enzyme granules can be coated with a protective coating during this process step, for example in order thus to mask or to change any possible intrinsic colour. To obtain light-coloured enzyme granules, for example, the enzyme granules can be coated in a manner known per se with a dispersion comprising titanium dioxide. For this, in a manner known per se, titanium dioxide can be dispersed in water with polyethylene glycol as a binder and the dispersion can be sprayed into the drying unit via nozzles.

Enzyme granules which largely consist of rounded dust-free particles having a diameter of 0.2 to 1.0 mm and a bulk density of 600 g/l to 1,100 g/l and which are preferably suitable as constituents of pulverulent detergents and cleaning agents are obtained by the process according to the invention.

The invention also relates to the use of the enzyme granules according to the invention in pulverulent detergents and cleaning agents. Such detergents and cleaning agents can be used, for example, for cleaning surfaces, for example for removing fat residues in the hygiene or foodstuffs sector. The enzyme granules according to the invention are preferably used in washing powder formulations for cleaning textiles or utensils. In addition to the enzyme granules, the washing powder formulations here can comprise all the detergent constituents which are customary per se in the prior art, such as surfactants, bleaching agents or builders, and other customary auxiliaries for formulation of pulverulent detergents in amounts customary per se. The auxiliaries include, for example, boosters, enzyme stabilizers, anti-redeposition agents and/or compatibilizing agents, complexing and chelating agents, foam regulators and additives such as optical brighteners, opacifying agents, corrosion inhibitors, anti-electrostatics, dyestuffs, bactericides, bleaching agents, activators and per-acid bleaching agent precursors. Thus, in addition to the enzyme granules according to the invention, the washing powder formulations can comprise bleaching agents or bleaching agent mixtures based on oxygen compounds, for example perborates such as sodium perborate tetrahydrate or sodium perborate monohydrate, in amounts customary per se.

The enzymes in the granules according to the invention are stabilized in a surprising manner by incorporation of a formate of an alkali metal or alkaline earth metal, if appropriate in combination with a reducing sugar. The enzyme granules according to the invention do display very good properties which are particularly suitable for use in pulverulent detergent formulations. In pulverulent detergent formulations, they have a very high storage stability, which renders them especially suitable in particular also for detergent formulations containing oxidizing agents, such as, for example, peroxide-containing detergent formulations. Because of their very low dust and enzyme dust content, the enzyme granules according to the invention are also distinguished by a very good process ability. Another advantage is that relatively large losses of enzymes can be avoided during the preparation according to the invention of the enzyme granules. Furthermore, the enzyme granules according to the invention have excellent solution properties during the washing operation. Thus, more than 90% of the enzyme is already released from the enzyme granules according to the invention into the washing solution within 2 minutes, so that a very long action time of the enzyme on the corresponding object to be cleaned, for example kitchen utensils or textiles, is guaranteed during the washing operation.

The following examples are intended to illustrate the invention further, but without limiting it in its scope.

EXAMPLES

Example 1

Preparation of Enzyme Granules

The preparation of enzyme granules which comprise a highly alkaline protease as the enzyme constituent is described in the following.

The activity of the proteases processed into the enzyme granules was determined in Delft Units (DU). 1,000 DU correspond to the proteolytic activity which, at a volume of 1 ml of a 2% strength enzyme solution (w/w), gives an extinction difference after breakdown of casein of 0.400 (1 cm light path; 275 nm; determination against a blank sample).

An aqueous enzyme concentrate, isolated in a manner known per se by fermentation of *Bacillus alcalophilus*, of a highly alkaline protease having a solid content of approximately 37% by weight and a proteolytic activity of approximately 950,000 DU/g was employed in the preparation of the enzyme granules.

A premix of the pulverulent constituents of the recipe was prepared in a cone mixer. For this, the following constituents were mixed with one another, based on the total solids contents of the enzyme granules:

water-insoluble fillers
23% by weight of cellulose
11% by weight of kaolin
6% by weight of calcium carbonate
21% by weight of wheat flour/starch mixture
(8% by weight of wheat flour, 13% by weight of starch)
water-soluble fillers
9% by weight of sodium sulphate
binders
11% by weight of polyethyleneglycol 3000
0.8% by weight of polyvinylpyrrolidone K-90
reducing sugars
4.5% by weight of lactose
alkaline earth metal formate
2.2% by weight of calcium formate The enzyme concentrate and water in an amount such that a homogeneous extrudable composition was formed were added to the pulverulent premix in the cone mixer. The moisture content of this moist mixture thus formed was about 30% by weight.

The resulting homogeneous moist mixture was transferred to an extruder. The composition was extruded to give extrudates through a perforated die having hole diameters of about 0.6 mm. The extrudate fragments thereby obtained were transferred to a rotary plate apparatus, where they were shaped to rounded particles during a working the of about 20 seconds. The rounded particles were then dried to a water content of about 5% at a temperature of about 48° C. in a fluidized bed dryer. They were also coated in the fluidized bed dryer in a manner known per se with a protective coating comprising an aqueous dispersion of titanium dioxide with polyethylene glycol as the binder.

The resulting granules consisted of rounded particles having diameters of 0.2 to 1.0 nm. The granules were non-tacky and readily pourable, with a bulk density of about 800 g/l.

Example 2 to 5

Preparation of Other Enzyme Granules

Aqueous enzyme concentrates obtained in a manner known per se by fermentation of the Bacillus alcalophilus, of a highly alkaline protease were also processed into the enzyme granules of Examples 2 to 5 in the same manner. The solids content of these enzyme concentrates was about 11.5% by weight, corresponding to a proteolytic activity of about 320,000 DU/g. The concentrations of the other constituents are stated in the following table, in each case based on the total solids content.

| Example No. | 2 | 3 | 4 | 5 |
|---|---|---|---|---|
| water-insoluble fillers [% by weight]: | | | | |
| Cellulose | 23.6 | 27.0 | 23.0 | 23.0 |
| Kaolin | — | 10.6 | 11.1 | 10.6 |
| Calcium carbonate | 8.8 | 10.4 | 10.4 | 6.0 |
| Bentonite | 16.6 | 9.0 | 8.9 | — |
| Wheat flour | 7.1 | — | — | 7.2 |
| Starch | — | 8.0 | — | 14.2 |
| water-soluble fillers [% by weight]: | 13.3 | 4.4 | 13.3 | 8.4 |
| sodium sulphate | | | | |
| Binder [% by weight]: | | | | |
| PEG 3000 | 10.8 | 10.8 | 10.8 | 10.8 |
| PVP K-90 | 1.3 | 1.3 | 1.3 | 1.3 |
| Diapersing auxiliary [% by weight]: | 0.4 | 0.4 | 0.4 | 0.4 |
| Sulphur succinic acid diester | | | | |
| Lactose [% by weight] | 4.4 | 4.4 | 7.1 | 4.4 |
| Calcium formate [% weight] | 2.2 | 2.2 | 2.2 | 2.2 |

The enzyme granules obtained according to Examples 2 to 5 were also coated with a protective coating of titanium dioxide with polyethylene glycol as the binder, as already described for Example 1.

Example 6

Solution Properties of the Enzyme Granules

The solution properties of the resulting enzyme granules were determined as follows.

200 ml of an aqueous 2% strength sodium tripolyphosphate solution were stirred in a 400 ml glass beaker at 22° C. with a mechanical blade stirrer at a constant speed of rotation of 700 revolutions per minute. The solution had a water hardness of 15° German hardness.

1 g of enzyme granules was added to the stirred solution, avoiding the formation of lumps. Samples were taken after 2, 3 and 5 minutes and were filtered over a suction filter (filter paper: Schleicher and Schüll 589). The proteolytic activity in the filtrates was then determined. The protease activity determined in the filtrates (measured in DU) was based on the enzyme activity contained in the enzyme granules added, the starting activity in 1 g of enzyme granules corresponding to 100% protease activity.

After 2 minutes, about 90% of protease was released from the granules from the enzyme granules prepared according to Example 1. The protease had been released to the extent of about 96% after 3 minutes and to the extent of 99% after 5 minutes.

Example 7

Storage Stability of the Enzyme Granules in the Presence of Constituents of Detergents An amount of 1.0% by weight, based on the detergent base formulation, of enzyme granules according to the invention was admixed to a perborate-containing detergent base formulation commercially obtainable for detergent manufacturers, which comprised 18.4% by weight of zeolite, 7.3% of sodium carbonate, 4.8% by weight of linear alkylbenzenesulphonate, 3.3% by weight of nonionic, 3.3% by weight of soap, 0.1% by weight of defoamer, 1.5% by weight of carboxymethylcellulose, 0.15% by weight of optical brightener, 3.8% by weight of sodium disilicate, 25% by weight of perborate tetrahydrate, 1.5% by weight of TAED and 30.85% by weight of sodium sulphate. This mixture was then transferred to cardboard boxes (size: 7×11.8×2 cm) coated with polyethylene, which was then stored in a climatically controlled cabinet at 35° C. at 80% relative atmospheric humidity. At the end of the storage time, samples were taken from the boxes and dissolved in sodium sulphite solution (10 g/l, pH 8.5), and the enzymatic activity was determined in a manner known per se using this solution.

After a storage time of 24 days, the enzymatic activity of the dissolved enzymatic detergent formulation was still 76%, based on the enzymatic activity originally present in the detergent formulation, such as was determined for the enzyme-containing detergent formulation in a measurement under identical conditions prior to the storage studies. This demonstrates the outstanding storage stability of the enzyme granules according to the invention in the presence of constituents of detergent.

We claim:

1. In enzyme granules comprising at least one enzyme, a water-insoluble filler, a water-soluble filler, and a binder, the improvement comprising an effective enzyme stabilizing amount of a formate of an alkali metal or alkaline earth metal.

2. Enzyme granules according to claim 1, wherein said formate is calcium formate.

3. Enzyme granules according to claim 1, further comprising an enzyme stability enhancing amount of at least one reducing sugar.

4. Enzyme granules according to claim 3, wherein said reducing sugar comprises at least one reducing disaccharides.

5. Enzyme granules according to claim 4, wherein said reducing sugar comprises at least one sugar selected from the group consisting of lactose and maltose.

6. Enzyme granules according to claim 1, wherein said enzyme comprises an enzyme or a mixture of enzymes selected from the group consisting of proteases, amylases, cellulases, hemicellulases, lipases and oxidoreductases.

7. Enzyme granules according to claim 1, wherein said water-insoluble filler comprises a mixture of at least two water-insoluble filler ingredients selected from the group consisting of cellulose, laminar silicates, cereal flour and starch.

8. Enzyme granules according to claim 1, wherein said water-soluble filler comprises at least one salt selected from the group consisting of alkali metal chlorides, alkali metal acetates, and alkali metal sulfates.

9. Enzyme granules according to claim 1, wherein said binder comprises a mixture of polyethylene glycol having an average molecular weight in the range from 200 to 10,000 and polyvinylpyrrolidone having an average molecular weight in the range from 12,000 to 3,000,000.

10. Enzyme granules according to claim 1, wherein said granules consist of particles having a particle size in the range from 0.2 to 1.0 mm.

11. A powdered detergent comprising enzyme granules according to claim 1, and at least one detergent ingredient.

12. A powdered detergent according to claim 11, wherein said at least one detergent ingredient is selected from the group consisting of surfactants, bleaching agents, detergent builders, detergent boosters, enzyme stabilizers, anti-redeposition agents, compatibilizing agents, complexing and chelating agents, foam regulators, optical brighteners, opacifying agents, corrosion inhibitors, anti-static agents, dyestuffs, bactericides, bleaching agents, activators and peracid bleaching agent precursors.

13. In a process for preparing enzyme granules, said process comprising the steps of:

forming an extrudable mixture comprising an enzyme concentrate, water, at least one water-soluble filler, at least one water-insoluble filler, and at least one binder;

extruding said extrudable mixture into particles;

rounding the extruded particles in a rounding apparatus; and drying the rounded particles;

the improvement comprising incorporating in said extrudable mixture prior to the extruding step an effective enzyme stabilizing amount of a formate of an alkali metal or alkaline earth metal.

14. A process according to claim 13, further comprising coating the dried particles with a protective coating.

15. A process according to claim 13, wherein an amount of said formate is incorporated the extrudable mixture such that the produced granules contain from 0.5 to 15% weight of said formate relative to their total solids content.

16. A process according to claim 13, wherein said extrudable mixture additionally comprises reducing sugars in an amount such that the produced granules contain from 0.5 to 20% by weight reducing sugars relative to their total solids content.

* * * * *

UNITED STATES PATENT AND TRADEMARK OFFICE
CERTIFICATE OF CORRECTION

PATENT NO : 5,739,091
DATED : April 14, 1998
INVENTOR(S) : Torsten W. Kiesser; Hubert A. Herrmann; Gerhard Konieczny-Janda It is certified that error appears in the above-identified patent and that said Letters Patent is hereby corrected as shown below:

column 3, line 6, delete "bentonitc" and substitute --bentonite--

In Claim 4, line 3, delete "s" after disaccharide.

Signed and Sealed this

Fourth Day of May, 1999

Attest:

Q. TODD DICKINSON

Attesting Officer     Acting Commissioner of Patents and Trademarks